United States Patent [19]
Varnau

[11] Patent Number: 5,531,669
[45] Date of Patent: Jul. 2, 1996

[54] CERVICAL BRACE WITH INTERLOCK ASSEMBLY

[75] Inventor: David Varnau, Lynnwood, Wash.

[73] Assignee: Center for Prosthetics Orthotics, Inc., Seattle, Wash.

[21] Appl. No.: 342,164

[22] Filed: Nov. 18, 1994

[51] Int. Cl.$^6$ .................................................. A61F 5/02
[52] U.S. Cl. ............................. 602/18; 602/17; 602/19
[58] Field of Search .................................. 602/18, 19, 32, 602/33, 35, 36, 17–19; 128/DIG. 23

[56] References Cited

U.S. PATENT DOCUMENTS

| | | | |
|---|---|---|---|
| 2,102,069 | 12/1937 | Hanicke | 602/18 |
| 3,224,439 | 12/1965 | Blair, Jr. | 602/18 |
| 3,620,211 | 10/1971 | Goodell et al. | 602/18 X |
| 3,724,452 | 4/1973 | Nitschke | 602/18 |
| 4,383,523 | 5/1983 | Schurman . | |
| 4,582,051 | 4/1986 | Greene et al. | 602/18 |
| 4,628,913 | 12/1986 | Lerman | 602/18 |
| 4,643,174 | 2/1987 | Horiuchi | 602/18 |
| 4,793,334 | 12/1988 | McGuinness et al. | 602/18 |
| 4,913,135 | 4/1990 | Mattingley | 602/18 |
| 5,005,563 | 4/1991 | Veale . | |
| 5,171,296 | 12/1992 | Herman . | |
| 5,433,696 | 7/1995 | Osti | 602/18 |

FOREIGN PATENT DOCUMENTS

| | | | |
|---|---|---|---|
| 317173 | 5/1989 | European Pat. Off. | 602/18 |
| 2126485 | 4/1984 | United Kingdom | 602/18 |

OTHER PUBLICATIONS

Article entitled "Cervical Orthoses: A study comparing their effectiveness in restricting cervical motion in normal subjects", by Rollin M. Johnson, MD., et al., appearing in the Journal of Bone and Joint Surgery, vol. 59A, No. 3, pp. 332–339, 1977.

Discussion and Acknowledgment as prior art of the C.D. Dennison Two Poster Cervical Collar and the Guilford Cervical Orthosis by Mr. David Varnau (the inventor of the cervical brace here disclosed and claimed) including information sheets with photographs of the Denison and Guilford devices (5 pages, unpublished).

*Primary Examiner*—Richard J. Apley
*Assistant Examiner*—Kim M. Lee
*Attorney, Agent, or Firm*—Graybeal Jackson Haley & Johnson

[57] ABSTRACT

A cervical brace including occipital and chin supports rigidly interconnected by rigid support bar means and interlocking assemblies in a manner maintaining such in fixed though adjustable position for fitting thereof to a patient. As the preferred form, a U-shaped support bar extends between an occipital support and a chin support with fastening means provided on each side of the chin support for releasably securing the legs of the support bar to the chin support. Adjustable stops are provided along the support bar legs.

9 Claims, 5 Drawing Sheets

5,531,669

1

CERVICAL BRACE WITH INTERLOCK ASSEMBLY

BACKGROUND OF THE INVENTION

1. Field of the Invention

The present invention relates to occipital and chin supports and more particularly to such supports which effectively fix the distance between the supports in the sagittal plane and prevent translation of the supports in the coronal plane.

2. Description of the Prior Art

Cervical-thoracic poster-type orthoses consist of an occipital support and a chin support attached to chest and/or back plates and it is common practice to connect the chin and occipital supports together by flexible means such as Velcro straps, as is characteristic of the support disclosed in Lerman U.S. Pat. No. 4,628,913. In such supports the straps, when anchored, only prevent the two supports from moving away from each other, i.e. prevent the chin support from moving anteriorly in relation to the occipital support. The flexible strap arrangement however, does not prevent the chin support from moving posteriorly which results in pressure on the patient's Adam's apple. Nor does the flexible strap arrangement prevent upward and downward translation of the chin support in relation to the occipital support. This limitation on the flexible strap connection in preventing cephalad, caudad, as well as posterior translation results in compromised head, and therefore, neck control and poor patient comfort.

Also known is the type of cervical brace disclosed in Nitschke U.S. Pat. No. 3,724,452 where a rigid chin support bar and a U-shaped occipital support bar are both secured to a chest plate, which arrangement often does not give the degree of occipital support desired since the respective supports are interconnected only through the chest plate and the only direct interlock between the occipital support and chin support is a flexible strap. As a result, one research study (see Rollin M. Johnson, MD., et al., "Cervical Orthoses: A study comparing their effectiveness in restricting cervical motion in normal subjects", Journal of Bone and Joint Surgery, Vol. 59A, No. 3, pp. 332–339, 1977), demonstrated that this cervical brace performs poorly in preventing cervical extension.

Another type of known cervical brace is that shown in Schurman U.S. Pat. No. 4,383,523 which discloses a cervical brace with independently adjustable chin and occipital supports which, although said to provide rigid support for each, is quite bulky and awkward to use, being designed for support based on pelvic contact rather than chest and back contact. In addition, although the distance between the chin and occipital supports in this brace can be fixed, the chin support may inadvertently shift cephalad or caudad in relation to the occipital support. This can occur because in this orthosis both the occipital support and the chin support pivot about separate axes on the lateral interlocking members.

McGuinness et al U.S. Pat. No. 4,793,334 discloses a cervical base with a chin support member which can be adjustably fixed either inwardly or outwardly but is without any occipital support.

Veale U.S. Pat. No. 5,005,563 discloses a brace which includes only an occipital support without a chin support and appears to be designed to create cervical traction.

Herman U.S. Pat. No. 5,171,296 discloses a head holding jig that is intended exclusively for use in surgery.

SUMMARY OF THE INVENTION

The cervical orthosis interlock assembly of the occipital and chin support of the present invention effectively fixes the distance between the supports in the sagittal plane. It likewise prevents the chin support from migrating cephalad or caudad in relation to the occipital support. These features offer a more effective and comfortable cervico-thoracic orthoses.

Among the many advantages of the cervical brace of the present invention are its construction so as to be readily disengageable for removal, its adjustability during fitting to establish and rigidly fix the exact spacial relationship between the chin and the occipital supports in the sagittal, frontal and coronal planes, and its construction enabling ease of on-patient adjustment of the spacial relationship of the chin and occipital supports. In the preferred form, the interlock assembly consists of a U-shaped support bar anchored to the occipital support and includes adjustable stops which fit into cooperating slots on the chin support for adjusting the anterior-posterior position and elevation of the chin support.

These and other objects, features and advantages of the invention are believed evident from the following description and accompanying drawings illustrating the preferred embodiment of the invention.

DESCRIPTION OF THE PREFERRED EMBODIMENT

Figure 1:
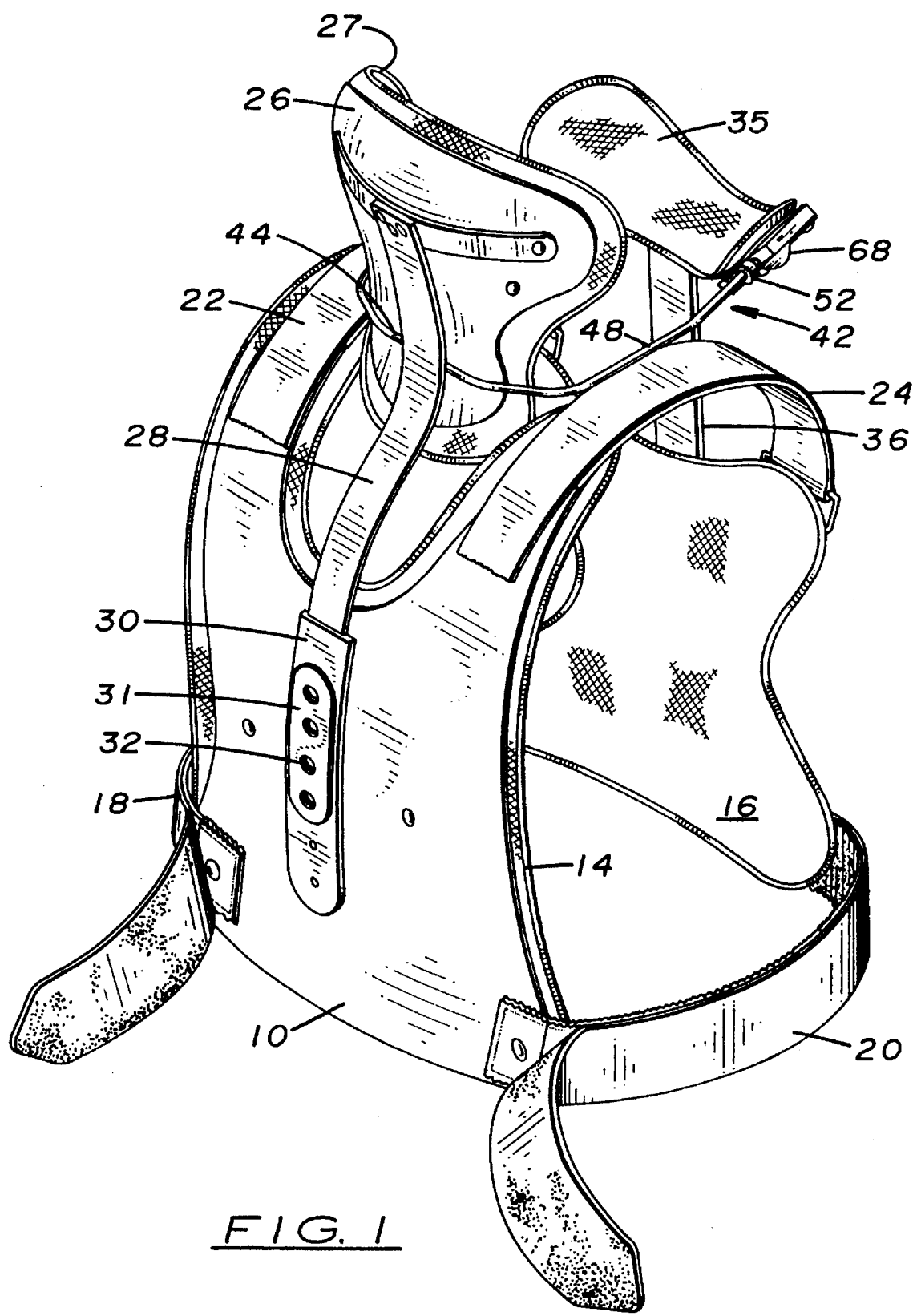
FIG. 1 is an isometric view from a somewhat upper aspect and a rearward right side aspect of the cervical brace which is the preferred embodiment of the invention.
Figure 2:
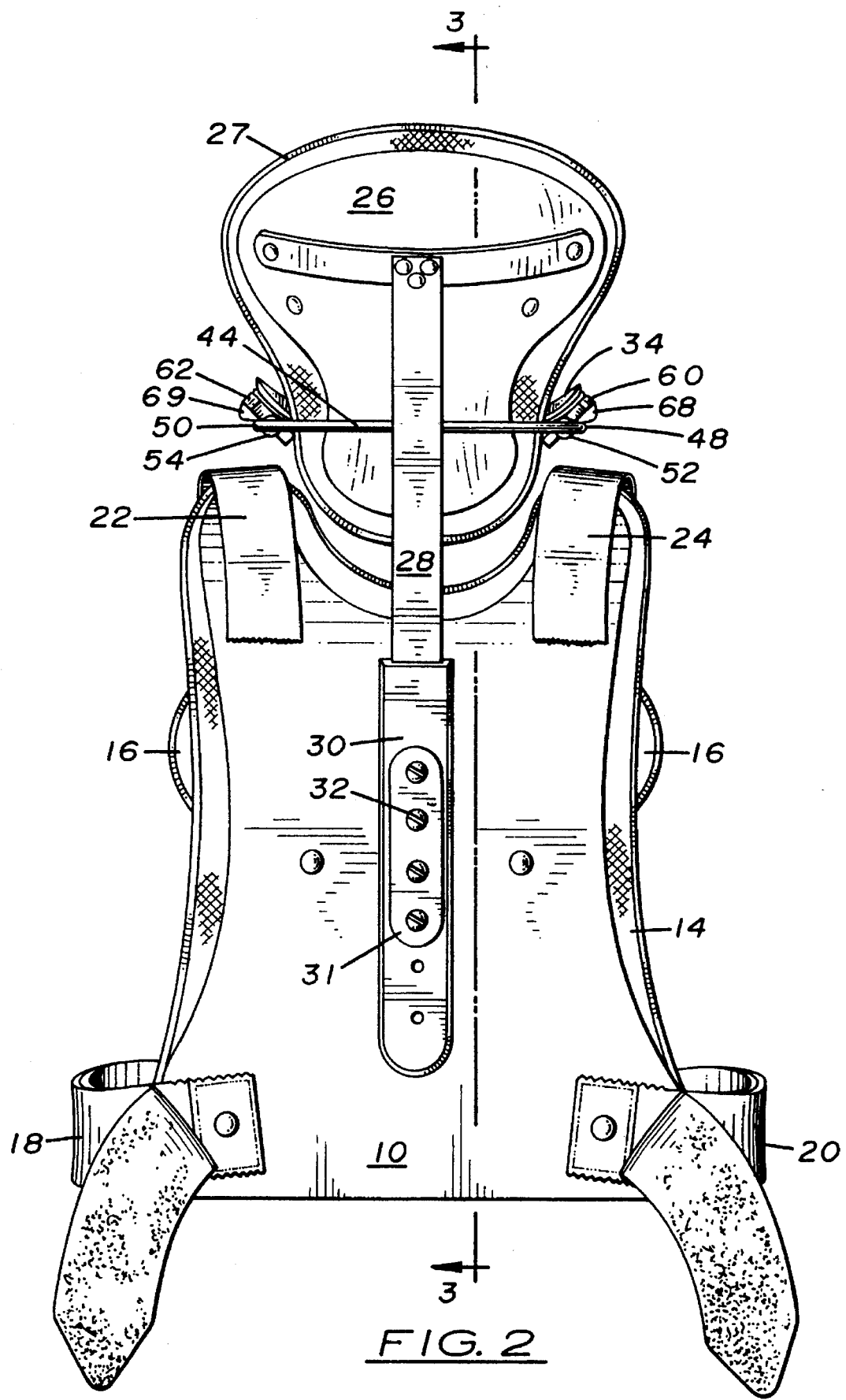
FIG. 2 is a rear elevational view thereof.

The cervical brace shown in FIGS. 1–4 comprises in general a back engaging plate 10 and a chest engaging plate 12 each formed preferably of molded plastic and each provided with a respective foam plastic lining 14, 16 for patient comfort. The body engaging plates 10, 12 are held in place on the patient by interconnecting Velcro waist straps 18, 20 and shoulder straps 22, 24.

Occipital support 26 with padding 27 is rigidly yet adjustably mounted on back plate 10 by means of generally vertically extending upright 28 which is lengthwise adjustable and fixedly retained in bracket 30 on the plate 10 by means of reinforcement strip 31 and threaded bolts 32. Similarly, chin support 34 with padding 35 is vertically adjustable on chest engaging plate 12 and vertically rigid with respect thereto by means of vertically extending upright 36 on the exterior of which is mounted plastic reinforcement strip 39, where upright 36 is adjustably yet fixedly retained in bracket 38 on chest plate 12 by threaded screws 40.

Figure 3:
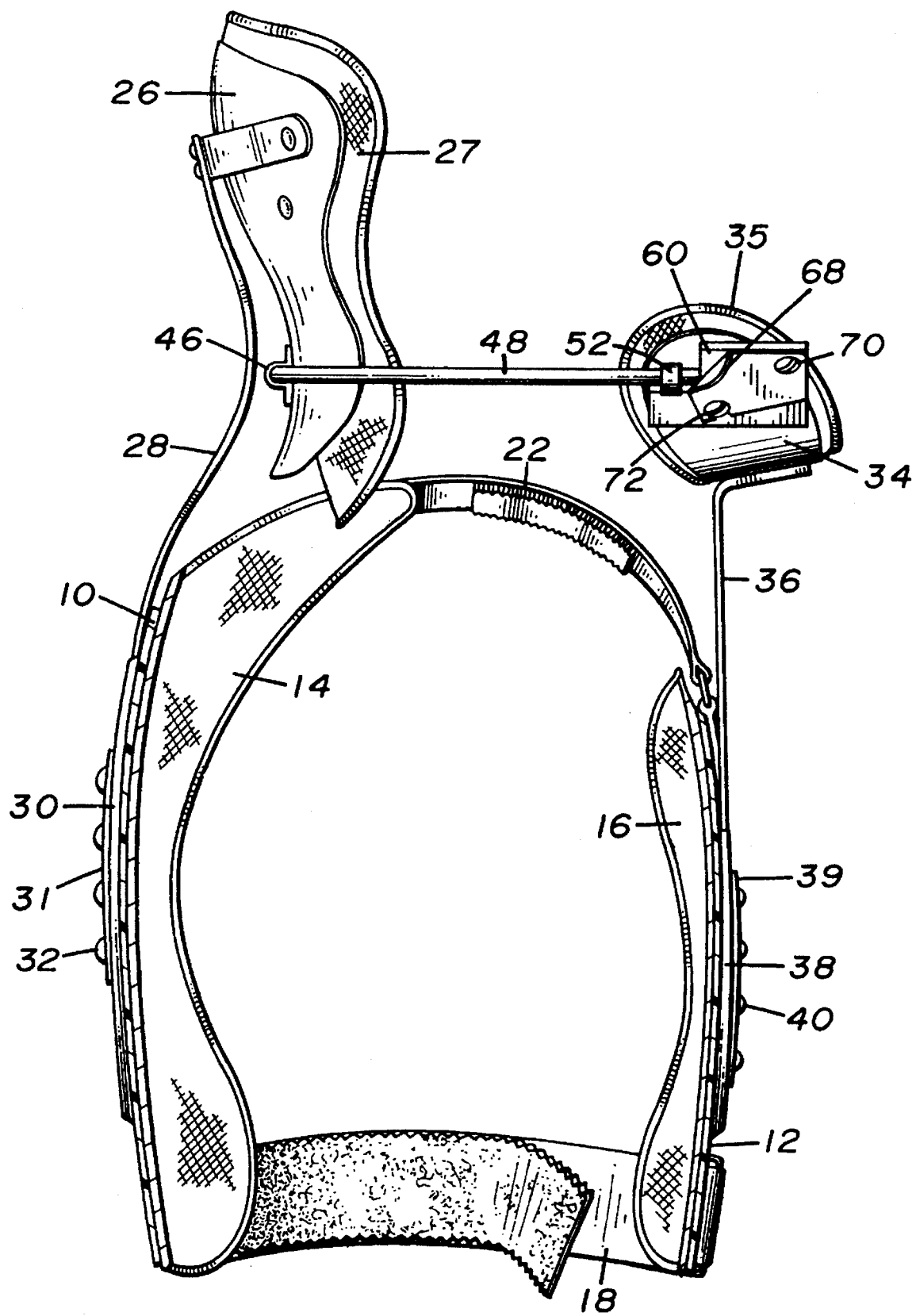
FIG. 3 is a right side elevational view, partly in cross section, thereof.
Figure 4:
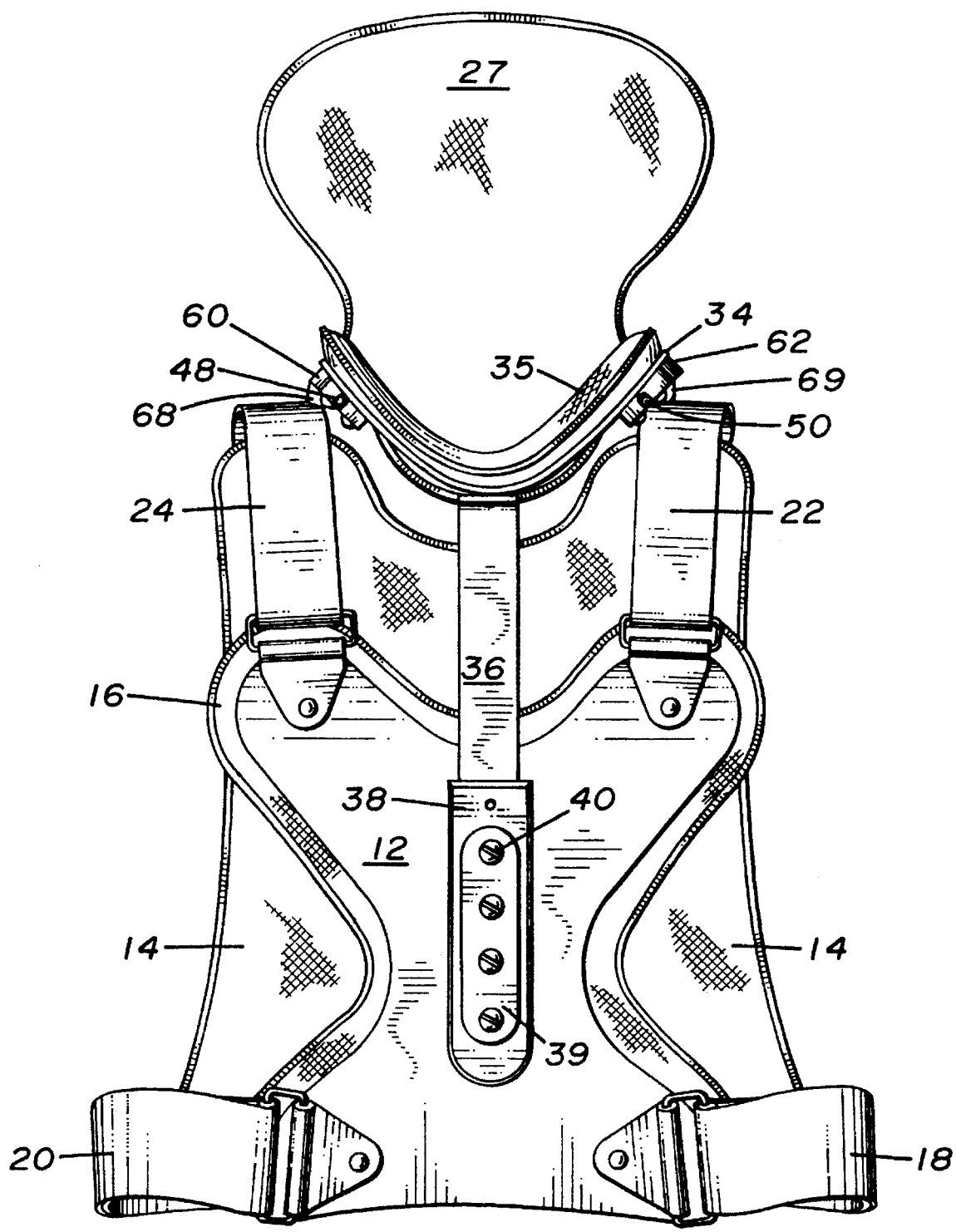
FIG. 4 is a front elevational view thereof.

In accordance with the invention, U-shaped support bar 42, which is anteriorly open and comprises a transverse cross member portion 44, is disposed against the reverse side of the occipital support 26 (FIG. 3). The cross member 44 is secured to the back of the occipital support by a bracket 46

Figure 5:
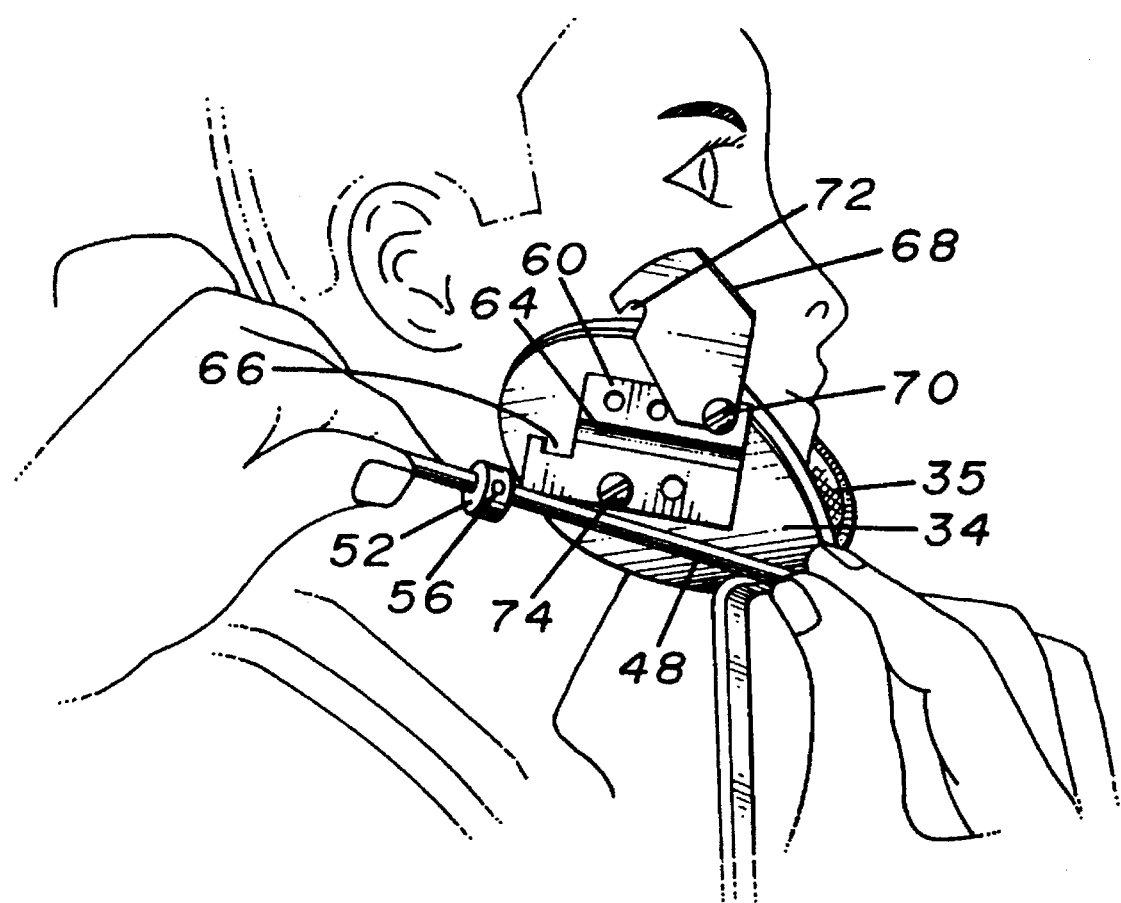
FIG. 5 is an enlarged detail view of one of the occipital support bar blocks and pivotally movable locking plates by means of which the brace is adjustably installed on a patient.

(FIG. 3). The support bar 42 is preferably an aluminum rod which may be contoured into a variety of shapes during fitting on the patient and which holds its contour following bending. It is preferably circular in transverse cross section with each leg 48, 50 carrying a respective annular stop 52, 54. Each of the stops 52, 54 is adjustable along and fixedly secureable to its respective support bar leg 48, 50 by a respective screw threaded fastener, one of which is shown at 56 in annular stop 52 on support bar leg 48 in FIG. 5. The fastener 56 and its like counterpart, not shown, in stop 54 is preferably an Allen head set screw. As will be evident, each annular stop 52 and its counterpart can be slid along the respective leg portion 48, 50 of the support bar 42. When the proper positions of each of these stops is determined in the course of installing the brace on a patient, the fasteners are tightened to keep the stops in fixed position relative to the support bar legs 48, 50. If desired, each leg 48, 50 of the support bar 42 can be scored in one or more locations near the respective ends thereof to permit breaking off the ends if excessively long support bar legs result from a given installation of the brace on a patient.

A pair of support blocks 60, 62, each of which is a mirror image of the other, are secured to the respective right and left sides of the chin support 34. They are preferably made of injection molded plastic material and formed to provide an elongated antereo-posteriorly extending channel, the channel 64 in right hand support block 60 being shown in FIG. 5. The inferior-posterior portion of each of the support blocks 60, 62 has a superiorly open slotted portion, with such slotted portion being indicated at 66 in right hand support block 60. Each of the support blocks 60, 62 has a relatively thin and flat locking plate pivotally secured adjacent to its superior edge by a respective fastener, such a locking plate and its fastener being shown in connection with support block 60 in FIG. 5 at 68 and 70, with the locking plate 69 being partly shown in FIG. 2 at 69. In use, the locking plates have respective slotted portions, such slotted portion being indicated at 72, which slotted portion 72 makes a friction fit under fastener 74 on the opposite side of the support block when the plate 68 slides over its channel 64. With the like stop 52 in place in the slots like slot 66 and with the outer adjacent portion of the support bar leg 48 in the channel 64 and the plate 68 pivoted down across the leg 48 and engaged with the slot 72 in contact with the fastener 74, the assembly provides a rigid innerlock between the occipital support 26 and the chin support 34. With the respective occipital and chin supports thus generally horizontally interlocked and also generally vertically fixed by reason of the rigid uprights 28 and 36 being prevented from translating cephalad and caudad in relation to each other, the patient is therefore more rigidly restrained and better protected from potentially painful or damaging cervical movements.

The interlock assembly is secured on the patient's orthosis by loosening the fasteners 56 of the stops 52, 54, moving the stops 52, 54 to the proper positions on the support bar legs 48, 50 and again tightening the screws on the stops 52, 54 to maintain them in fixed position on the bar legs 48, 50. In the course of this adjustment, the support bar legs 48, 50 can be bent into a configuration which permits them to extend around the patient's neck to the sides of the chin support 34, with the occipital support 26 in place against the patient's occiput. Thus the patient's neck is straddled by the right and left legs 48, 50 of the support bar 42. The support bar 42 extends from the occipital support 26 over the patient's shoulders to the chin support 34. The stops 52, 54 on the support bar legs 48, 50 are then inserted in the notched portions 66 of the support blocks 60, 62 and the end portions 48, 50 of the support bar 42 are positioned in the respective channel 64 in support block 60 and its counterpart in support block 62. The locking plates 68 and 69 are then swung over the channels and locked under the fastener 74, support block 60 and its counterpart in block 62 to hold the chin support 34 in a fixed position in relation to the patient's occipital support 26.

From the foregoing, various modifications and adaptations of the cervical brace components and particularly the interlocking assemblies thereof which are characteristic of the invention will occur to those skilled in the art to which the invention is addressed, within the scope of the following claims.

What is claimed is:

1. A cervical brace, comprising back and chest plates with interconnecting strap means to hold them in fixed position on the torso of a patient, an occipital support fixedly mounted on said back plate, a chin support fixedly mounted on said chest plate, elongate, rigid support bar means pivotally secured in the coronal plane directly to said occipital support and extending over the shoulders of a patient to said chin support, and means rigidly and adjustably connecting and securing the support bar means directly to the chin support and holding the chin support in fixed position relative to the occipital support during use.

2. Apparatus according to claim 1, wherein said support bar means includes a pair of laterally spaced apart legs extending transversely from said occipital support over the shoulders of the patient, and said means rigidly and adjustably connecting and securing the support bar means directly to the chin support includes fastening means on each side of said chin support releasably connecting and securing said legs directly to said chin support, said fastening means including means for varying the fixed distance between said occipital support and said chin support.

3. Apparatus according to claim 2, wherein each said leg has an adjustable stop secured to it, and wherein each said fastening means comprises a channel in the side of said chin support, a notch adjacent to said channel for receiving a respective said stop, and a locking plate pivotally secured to said side of said chin support to slide over the portion of said leg in each said channel to maintain the associated said stop fixed in its said notch and the leg in its channel and thereby rigidly interconnect said occipital support and said chin support.

4. Apparatus according to claim 1, wherein said support bar means includes a pair of laterally spaced apart rigid legs adapted to extend from said occipital support over the shoulders of a patient, wherein said brace includes pivotally releasable fastening means on each side of said chin support releasably securing said legs directly to said chin support, and wherein said fastening means includes means for adjusting the distance between said occipital support and said chin support and means for rigidly interconnecting said occipital support and said chin support.

5. Apparatus according to claim 4, wherein said fastening means for each said leg of said support bar means comprises an adjustable stop secured thereto, and also comprises a notch in said chin support for receiving a respective said stop, an elongate channel on each side of said chin support adjacent said notch for receiving a respective said leg, and a locking plate hinged to said chin support to slide over the portion of said leg in each said elongate channel to maintain the associated said stop fixed in its respective said notch and thereby rigidly interconnect said occipital support and said chin support.

6. Apparatus according to claim 5, wherein each said leg has an adjustable said stop secured to it; and wherein each said fastening means comprises a said notch in said chin support for receiving a respective said stop, a said elongate channel on each side of said chin support adjacent to said notch for receiving a respective said leg, and a separate said locking plate pivotally secured to the side of said chin support to slide over the portion of the said leg in each said channel to maintain the associated said stop fixed in its respective said notch and thereby maintain said chin support in fixed position relative to the said occipital support.

7. Apparatus according to claim 4, wherein said legs are fabricated of a round aluminum rod and of a nature to be contoured into a variety of shapes by bending during fitting of the brace on a patient.

8. Apparatus according to claim 7, comprising means for adjustment of the height of said occipital support on said back plate, and means for adjustment of the height of said chin support on said chest plate, and also comprising means for independently adjusting the length and configuration of the legs of said support bar means relative to the connections thereof with said chin support.

9. A cervical brace comprising:

a back plate, an occipital support adjustably mounted in fixed position on said back plate, a chest plate, a chin support adjustably mounted in fixed position on said chest plate, support bar means directly and adjustably interconnecting said occipital support and said chin support including pivot connection means directly connecting and securing said support bar means to said occipital support and interlock means directly and rigidly interconnecting said support bar means with said chin support, each of the occipital support mounting means, chin support mounting means, and support bar means interconnecting the occipital support and chin support being independently adjustable in the coronal and sagittal planes and fixedly securable in the desired position during the course of fitting the cervical brace to a patient.

* * * * *